US010606345B1

(12) United States Patent
Chou et al.

(10) Patent No.: US 10,606,345 B1
(45) Date of Patent: Mar. 31, 2020

(54) REALITY INTERACTIVE RESPONDING SYSTEM AND REALITY INTERACTIVE RESPONDING METHOD

(71) Applicant: XRSpace CO., LTD., Taoyuan (TW)

(72) Inventors: Peter Chou, Taipei (TW); Feng-Seng Chu, New Taipei (TW); Cheng-Wei Lee, Keelung (TW); Yu-Chen Lai, Taoyuan (TW); Chuan-Chang Wang, Taipei (TW)

(73) Assignee: XRSpace CO., LTD., Taoyuan (TW)

( * ) Notice: Subject to any disclaimer, the term of this patent is extended or adjusted under 35 U.S.C. 154(b) by 0 days.

(21) Appl. No.: 16/140,552

(22) Filed: Sep. 25, 2018

(51) Int. Cl.
| | | |
|---|---|---|
| *G06F 3/01* | (2006.01) | |
| *G06F 9/448* | (2018.01) | |
| *A63F 13/55* | (2014.01) | |
| *G06F 16/90* | (2019.01) | |

(52) U.S. Cl.
CPC .............. *G06F 3/011* (2013.01); *A63F 13/55* (2014.09); *G06F 9/4498* (2018.02); *G06F 16/90* (2019.01)

(58) Field of Classification Search
CPC .......... G06F 3/017; G06F 3/011; G06F 3/167; G06F 3/0488; G06F 3/04883; G06F 3/0484; G06F 3/0481; G06F 3/041–048
See application file for complete search history.

(56) References Cited

U.S. PATENT DOCUMENTS

| | | | |
|---|---|---|---|
| 2008/0300055 A1* | 12/2008 | Lutnick | G07F 17/3209 463/39 |
| 2011/0093820 A1* | 4/2011 | Zhang | A63F 13/06 715/863 |
| 2013/0051547 A1 | 2/2013 | Chavez | |
| 2013/0278501 A1* | 10/2013 | Bulzacki | G06F 3/017 345/157 |
| 2014/0047316 A1* | 2/2014 | Strydom | G06F 3/0481 715/233 |
| 2014/0073435 A1 | 3/2014 | Liu | |
| 2014/0270108 A1 | 9/2014 | Riahi | |
| 2017/0228034 A1* | 8/2017 | Hollar | G06F 3/017 |
| 2018/0068173 A1* | 3/2018 | Kolleri | G06K 9/00288 |
| 2018/0322870 A1 | 11/2018 | Lee | |
| 2019/0236416 A1* | 8/2019 | Wang | G06F 3/017 |

FOREIGN PATENT DOCUMENTS

| | | |
|---|---|---|
| TW | 486638 | 5/2002 |
| TW | 201312485 A1 | 3/2013 |

\* cited by examiner

*Primary Examiner* — Sanjiv D. Patel
(74) *Attorney, Agent, or Firm* — Winston Hsu

(57) ABSTRACT

A reality interactive responding system, comprising a first server configured to receive first input data from a user and to determine whether the first input data conform to any one of a plurality of variation conditions or not; and a second server coupled to the first server and configured to receive second input data from the first server when the first input data conform to any one of the plurality of variation conditions and to determine a plurality of interactions in response to the first input data from the user; wherein the first input data from the user are related to an action, a facial expression, a gaze, a text, a speech, a gesture, an emotion or a movement generated by the user.

6 Claims, 3 Drawing Sheets

REALITY INTERACTIVE RESPONDING SYSTEM AND REALITY INTERACTIVE RESPONDING METHOD

BACKGROUND OF THE INVENTION

1. Field of the Invention

The present invention relates to a reality interactive responding system and a reality interactive responding method, and more particularly, to a reality interactive responding system and a reality interactive responding method capable of fusing a game AI with an interactive AI.

2. Description of the Prior Art

With the advancement and development of technology, the demand of interactions between a computer system and a user is increased. Human-computer interaction technology, e.g. somatosensory games, virtual reality (VR) environment, augmented environment (AR) and extended reality (XR) environment, becomes popular because of its physiological and entertaining function. In the above stated virtual environments, a non-player character (NPC) is created to help the user, such as an NPC avatar. The NPC is embedded with a game artificial intelligence (AI) which enables the NPC to interact with the user, such as, replying or reacting to simple messages or questions from the user, but the current NPC can only reply simple questions or machine responses, which is restricted to texts or words in the virtual environment.

However, since the user may express in all kinds of methods in the virtual environment, e.g. speech, facial expression, body movement and gesture. Under this situation, the NPC in the virtual environment, which is not capable of being interactive with the user or being a humanlike NPC, affects the user experience.

SUMMARY OF THE INVENTION

Therefore, the present invention provides a reality interactive responding system and a reality interactive responding method to improve the NPC in the virtual environment to be more interactive to the user and provide a better user experience.

The present invention discloses a reality interactive responding system, comprising a first server configured to receive first input data from a user and to determine whether the first input data conform to any one of a plurality of variation conditions or not; and a second server coupled to the first server and configured to receive second input data from the first server when the first input data conform to any one of the plurality of variation conditions and to determine a plurality of interactions in response to the first input data from the user; wherein the first input data from the user are related to an action, a facial expression, a gaze, a text, a speech, a gesture, an emotion or a movement generated by the user.

The present invention further discloses an interactive responding method, for a reality interactive responding system, comprising a first server receiving a first input data from a user and determining whether the first input data conform to any one of a plurality of variation conditions or not; and a second server receiving second input data from the first server when the first input data conform to any one of the plurality of variation conditions and to determine a plurality of interactions in response to the first input data from the user; wherein the first input data from the user are related to a an action, a facial expression, a gaze, text, a speech, a gesture, an emotion or a movement generated by the user.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
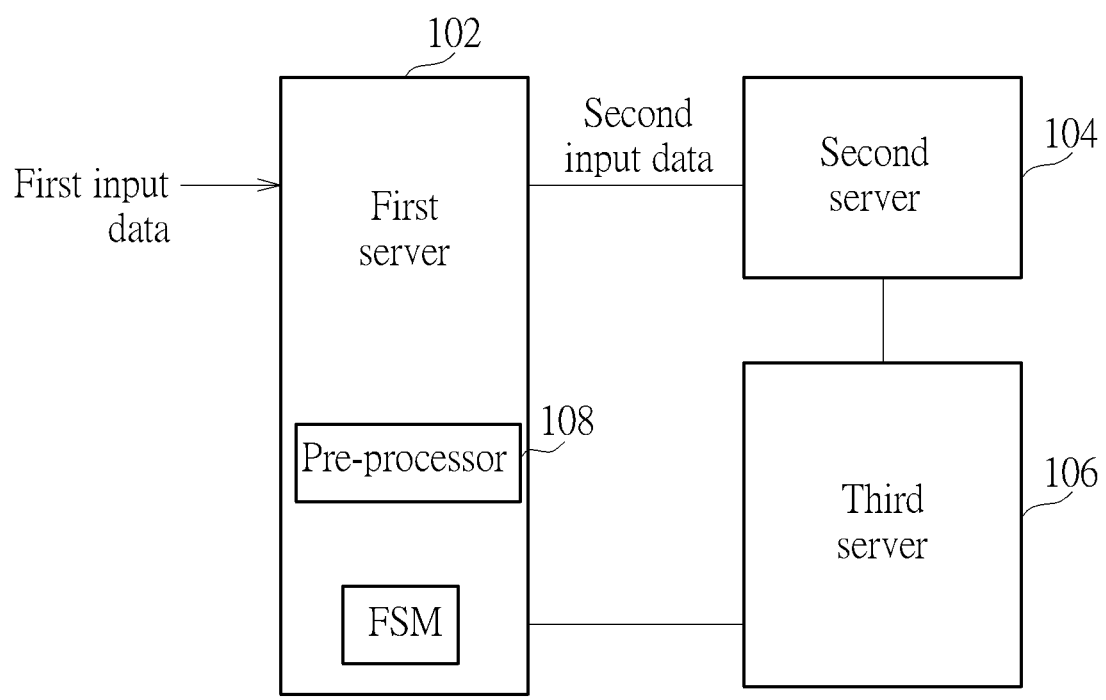
FIG. 1 is a schematic diagram of a reality interactive responding system according to an embodiment of the present invention.

Please refer to FIG. 1, which is a schematic diagram of a reality interactive responding system 10 according to an embodiment of the present invention. The reality interactive responding system 10 includes a first server 102, a second server 104 and a third server 106. The first server 102 is configured to receive first input data from a user and to determine whether the first input data conform to any one of a plurality of variation conditions or not. In an embodiment, the first server 102 may be a game AI server, which receives information from the user in a virtual environment, such as actions, facial expressions, gazes, texts, speeches, messages, body gestures or body movements generated by the user, and then, the game AI server determines whether the information generated by the user conforms to the variation conditions or not. The second server 104 is configured to receive second input data from the first server 102 when the first input data conform to the variation conditions, and to determine a plurality of interactions in response to the first input data from the user. Notably, the first input data and second input data might be the same. In an embodiment, the second server 104 may be a Chatbot server, which determines the interactions in response to the actions, facial expressions, gazes, texts, speeches, messages, body gestures or body movements generated by the user. After the interactions are determined, the first server 102 displays a plurality of actions corresponding to the interactions via a non-player character (NPC). The third server 106 may include a data application programming interface (API) server to retrieve and store a plurality of the states of the user and the NPC for the interactions in response to the first input data. In detail, the third server 106 stores the states of the user corresponding to the interactions displayed via the non-player character, such as a friendship value between the user and NPC, a sport preference value of the user or a happiness value of the NPC. In an embodiment, the third server 106 may store that the user prefers soccer to basketball into a database. Therefore, the reality interactive responding system 10 of the present invention coordinates the game AI server (i.e. the first server 102) with the Chatbot server (i.e. the second server 104) to interact with the user via the NPC with speeches, facial expressions, body movements and gestures.

The examples mentioned above briefly explain that the reality interactive responding system 10 of the present invention provides a more intelligent and interactive method to communicate with the user in the virtual environment. Notably, those skilled in the art may make proper modifications. For example, the first server 102 and the second server 104 are not limited to be implemented by the game AI server and the Chatbot server, and other kinds of servers, which may analyze or understand the information generated by the user, may be adopted to determine the interactions and actions in response to the user, and not limited thereto.

Figure 2:
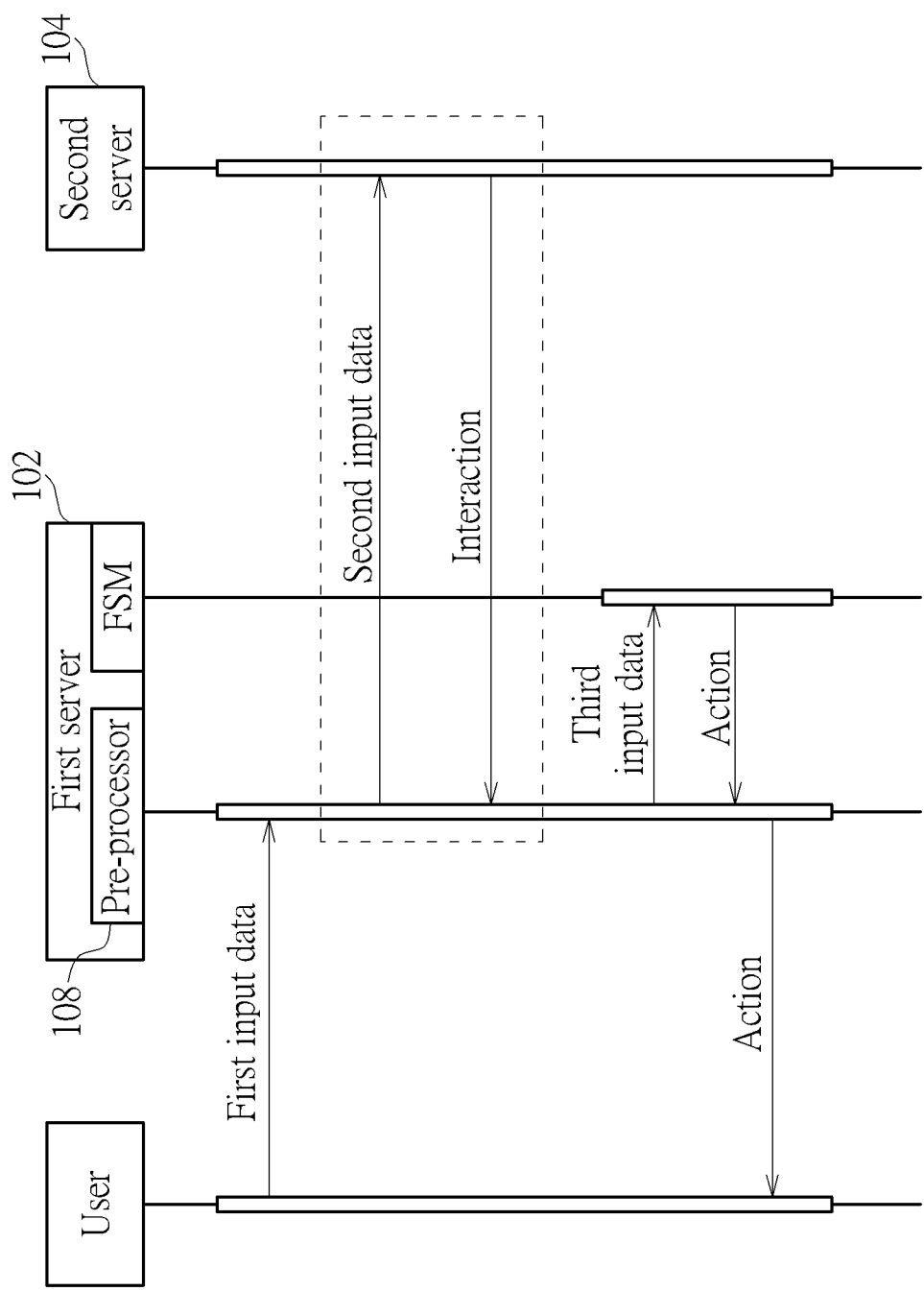
FIG. 2 is a schematic diagram of an operation process of the reality interactive responding system according to an embodiment of the present invention.

In detail, the first server 102 includes a pre-processor 108 and a finite state machine FSM. The pre-processor 108 generates third input data according to the first input data and the interactions generated by the second server 104. The FSM changes a plurality of states according to the third input data, wherein the states correspond to the interactions. More specifically, please refer to FIG. 2, which is a schematic diagram of an operation process of the reality interactive responding system 10 according to an embodiment of the present invention. The first server 102 receives the first input data made by the user, such as speeches, movements or gestures, and then, the first server 102 determines whether the first input data conform to any one of the variation conditions, such as, whether a distance between the user and the NPC in the virtual environment is less than 1 meter. When the variation condition is satisfied, i.e. the distance between the user and the NPC is less than 1 meter, the first server 102 transfers the second input data to the second server 104. And the second server 104 determines the interactions in response to the first input data according to the speeches, movements or gestures made by the user. In an embodiment, the third server 106 memorizes the interactions corresponding to the first input data determined by the second server 104, and updates the interactions with the first server 102 and the second server 104. After the pre-processor 108 receives the interactions corresponding to the first input data form the second server 104, the pre-processor 108 generates the third input data. The FSM of the first server 102 further generates the corresponding actions and controls the NPC to display the corresponding actions to the user when the state of the FSM is changed according to the third input data, e.g. an emotion state of the FSM is changed from happy to angry. Moreover, the FSM updates the states of the FSM to the first server 102. In this way, the user may interact with the NPC in a more interactive way in the virtual environment. Notably, the first input data from the user are related to a text, a speech, a movement, a gesture or an emotion generated by the user, and not limited thereto.

In another embodiment, when the first input data made by the user do not conform to any one of the variation conditions, the FSM of the first server 102 may directly evaluate the first input data and generate corresponding actions thereto. More specifically, when the user asks the NPC essential questions, such as commands, self-introduction or road direction, the FSM of the first server 102 may directly look up the third server 106 for reference and determine the corresponding actions to the questions. In an embodiment, when the user asks the reality interactive responding system 10 to play music or video, the FSM of the first server 102 may directly generate the corresponding actions and play music or video. In this example, the first server 102 does not transfer the first input data to the second server 104 for further determination of interactions, since none of the variation conditions is satisfied.

Since the first input data generated by the user are related to the text, speech, movement, gesture or emotion of the user, the second server 104 of the reality interactive responding system 10 may control the actions or the emotions displayed via the NPC accordingly. In a usage scenario of the virtual environment, when the user actively walks to the NPC and chat or when the user stays still and stares at the NPC for over 6 seconds, the pre-processor 108 determines that the NPC actively walks to the user and chat according to the states of the FSM. Alternatively, when the user walks by the NPC for more than 3 times, the pre-processor 108 determines that the NPC actively walks to the user and asks the user for a reason accordingly.

In addition to the actions stated above, the FSM may determine actions with the user by gestures, movements or emotions. In an example, when the user is too far from the NPC, the FSM may determine the action about asking the user to stay closer to the NPC with a movement of waving hands. In another example, when the user attempts to touch or contact the NPC in the virtual environment, the FSM may determine the actions of stopping the user with a speech or shunning the user with anger. Or, in still another example, the FSM may determine the actions of covering a mouth of the NPC when agreeing with the user.

Figure 3:
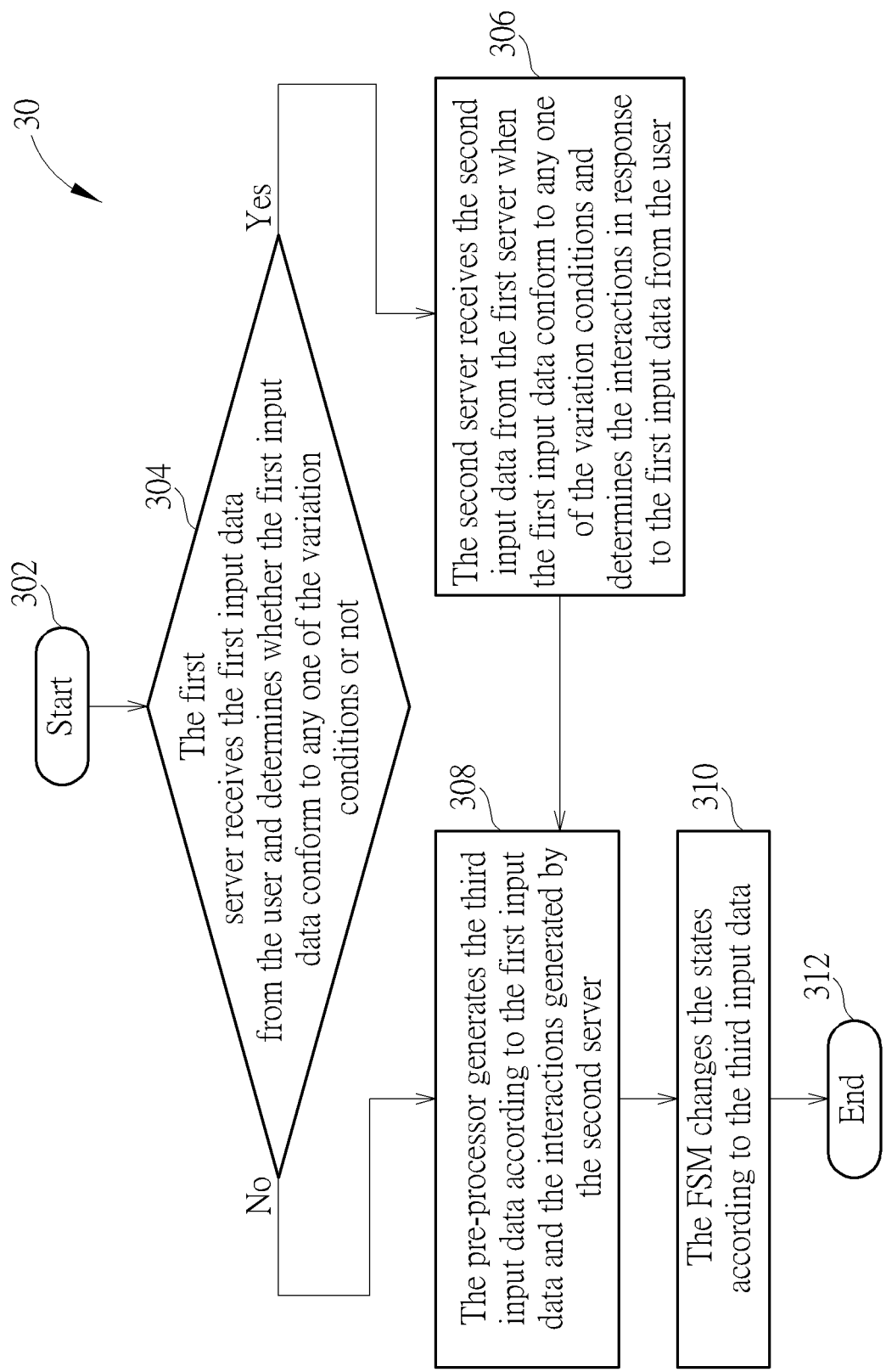
FIG. 3 is a schematic diagram of a reality interactive responding process according to an embodiment of the present invention.

Based on different applications and design concepts, the reality interactive responding system 10 of the present invention may be implemented in all kinds of methods. Furthermore, the operating process of the reality interactive responding system 10 may be concluded to a reality interactive responding method 30 as shown in FIG. 3, which includes the following steps:

Step 302: Start.

Step 304: The first server 102 receives the first input data from the user and determines whether the first input data conform to any one of the variation conditions or not. If yes, execute step 306; if no, execute step 308.

Step 306: The second server 104 receives the second input data from the first server 102 when the first input data conform to any one of the variation conditions and determines the interactions in response to the first input data from the user.

Step 308: The pre-processor 108 generates the third input data according to the first input data and the interactions generated by the second server 104.

Step 310: The FSM changes the states according to the third input data.

Step 312: End.

The details of the interactive responding process 30 may be referred to the above mentioned embodiments of the reality interactive responding system 10 and are not narrated herein for brevity.

Notably, the embodiments stated above illustrate the concept of the present invention, those skilled in the art may make proper modifications accordingly, and not limited thereto. For example, the variation conditions may be varied or be adjusted according to indications of a user or a manufacturer, or settings of a computer system, the interactions or the actions stored in a database DB of the third server, and not limited thereto, which all belongs to the scope of the present invention.

In summary, the present invention provides a reality interactive responding system and a reality interactive responding method to improve the NPC in the virtual environment to be more interactive to the user, such that the NPC may interact with the user with involvements of speeches, body gestures and emotions and provide a better user experience.

Those skilled in the art will readily observe that numerous modifications and alterations of the device and method may be made while retaining the teachings of the invention.

Accordingly, the above disclosure should be construed as limited only by the metes and bounds of the appended claims.

What is claimed is:

1. A reality interactive responding system, comprising:
a first server configured to receive first input data from a user in a virtual environment and to determine whether the first input data conform to any one of a plurality of variation conditions or not, wherein the first input data from the user are related to an action, a facial expression, a gaze, a text, a speech, a gesture, an emotion or a movement generated by the user in the virtual environment; and
a second server coupled to the first server and configured to receive second input data from the first server when the first input data conform to any one of the plurality of variation conditions and to determine a plurality of interactions in response to the first input data from the user;
wherein the first server comprises a pre-processor and a finite state machine, the pre-processor is configured to generate third input data according to the first input data and the plurality of interactions generated by the second server, the finite state machine is configured to change a plurality of states according to the third input data, the first server is further configured to display the plurality of actions, facial expressions, gazes, texts, speeches, gestures, emotions or movements via a non-player character in the virtual environment.

2. The reality interactive responding system of claim 1, further comprising:
a third server coupled to the second server and configured to retrieve and store the plurality of actions, interactions, a plurality of NPC states and a plurality of user states in response to the first input data.

3. The reality interactive responding system of claim 2, wherein the third server updates the plurality of actions, interactions, NPC states and user states in response to the first input data with the first server and the second server.

4. A reality interactive responding method, for a reality interactive responding system, comprising:
a first server receiving first input data from a user in a virtual environment and determining whether the first input data conform to any one of a plurality of variation conditions or not, wherein the first input data from the user are related to a an action, a facial expression, a gaze, text, a speech, a gesture, an emotion or a movement generated by the user in the virtual environment;
a second server receiving second input data from the first server when the first input data conform to any one of the plurality of variation conditions and to determine a plurality of interactions in response to the first input data from the user;
a pre-processor of the first server generating third input data according to the first input data and the plurality of interactions generated by the second server;
a finite state machine of the first server changing a plurality of states according to the third input data, wherein the plurality of states correspond to a plurality of actions; and
the first server displaying the plurality of actions, facial expressions, gazes, texts, speeches, gestures, emotions or movements via a non-player character in the virtual environment.

5. The reality interactive responding method of claim 4, further comprising:
a third server retrieving and storing the plurality of actions, interactions, a plurality of NPC states and a plurality of user states in response to the first input data.

6. The reality interactive responding method of claim 5, wherein the third server updates the plurality of actions, interactions, NPC states and user states in response to the first input data with the first server and the second server.

* * * * *